US008732601B2

(12) United States Patent
Licato et al.

(10) Patent No.: US 8,732,601 B2
(45) Date of Patent: May 20, 2014

(54) CLINICAL REVIEW AND ANALYSIS WORK FLOW FOR LUNG NODULE ASSESSMENT

(75) Inventors: Paul E. Licato, Wauwatosa, WI (US); Beth A. Heckel, Sturtevant, WI (US); Saad Ahmed Sirohey, Pewaukee, WI (US); Matthieu Denis Ferrant, Wezembeek-Oppem (BE); Bob L. Beckett, Waukesha, WI (US)

(73) Assignee: General Electric Company, Schnectady, NY (US)

( * ) Notice: Subject to any disclaimer, the term of this patent is extended or adjusted under 35 U.S.C. 154(b) by 610 days.

(21) Appl. No.: 11/162,672

(22) Filed: Sep. 19, 2005

(65) Prior Publication Data

US 2007/0064982 A1    Mar. 22, 2007

(51) Int. Cl.
*G06F 3/048*    (2013.01)

(52) U.S. Cl.
USPC .......................... 715/771; 715/850; 382/128

(58) Field of Classification Search
USPC .......................... 715/771, 772, 850; 382/128
See application file for complete search history.

(56) References Cited

U.S. PATENT DOCUMENTS

| | | | |
|---|---|---|---|
| 6,049,622 A * | 4/2000 | Robb et al. .................... 382/128 |
| 6,675,039 B2 * | 1/2004 | Heckel et al. ................. 600/425 |
| 7,296,239 B2 | 11/2007 | Shen et al. |
| 2002/0070970 A1 * | 6/2002 | Wood et al. .................... 345/766 |
| 2002/0097902 A1 | 7/2002 | Roehrig et al. |
| 2003/0018245 A1 | 1/2003 | Kaufman et al. |
| 2003/0035507 A1 | 2/2003 | Hsu et al. |
| 2003/0164860 A1 | 9/2003 | Shen et al. |
| 2005/0002548 A1 * | 1/2005 | Novak et al. .................. 382/128 |
| 2005/0010445 A1 * | 1/2005 | Krishnan et al. .................. 705/2 |
| 2005/0065424 A1 * | 3/2005 | Shah et al. .................... 600/407 |
| 2005/0102315 A1 | 5/2005 | Krishnan ...................... 707/102 |
| 2005/0107689 A1 | 5/2005 | Sasano |
| 2005/0197567 A1 * | 9/2005 | Qian et al. .................... 600/425 |
| 2005/0228250 A1 | 10/2005 | Bitter et al. |
| 2006/0079743 A1 | 4/2006 | Ferrant et al. |

FOREIGN PATENT DOCUMENTS

| | | |
|---|---|---|
| JP | 10-500321 A | 1/1998 |
| JP | 2001525581 A | 12/2001 |
| JP | 2003522343 A | 7/2003 |
| JP | 2003-265463 A | 9/2003 |
| JP | 2005-518916 A | 6/2005 |
| JP | 2005-198890 A | 7/2005 |
| WO | 9526682 A1 | 10/1995 |
| WO | 9928857 A1 | 6/1999 |
| WO | 9963478 A1 | 12/1999 |

(Continued)

OTHER PUBLICATIONS

Netherlands Search Report; Netherlands Application No. 1032508; Jan. 30, 2008.

(Continued)

*Primary Examiner* — Steven Sax
*Assistant Examiner* — Christopher J Fibbi

(57) ABSTRACT

An image display system includes user configurable viewports for the review and analysis of image data. The user configurable viewports include a review viewport and an analysis viewport. The review viewport displays in a review mode, a plurality of image views of the image data. The analysis viewport displays in an analysis mode, a plurality of image views of the image data. The review viewport and the analysis viewport may be configured for simultaneous display of related image data.

19 Claims, 5 Drawing Sheets

(56) References Cited

FOREIGN PATENT DOCUMENTS

| WO | 02056240 A1 | 7/2002 |
|---|---|---|
| WO | 03101303 A1 | 12/2003 |
| WO | 2004/070648 A | 8/2004 |
| WO | 2005072131 A2 | 8/2005 |

OTHER PUBLICATIONS

Japanese Office Action for JP2006-240238 dated Dec. 6, 2011; 6 pgs.
Unofficial translation of Japanese Official Action from JP Application No. 2006-240238 dated Mar. 12, 2013.

* cited by examiner

CLINICAL REVIEW AND ANALYSIS WORK FLOW FOR LUNG NODULE ASSESSMENT

BACKGROUND OF THE INVENTION

This invention relates generally to display systems and specifically to an image data display system for the review and analysis of medical data.

Visualization of anatomical data acquired by imaging devices generating 3D datasets is typically handled by volume rendering the intensity and/or density values (for example, Hounsfield Units (HU) in the case of Computed Tomography (CT) for instance). Many clinical applications are based on three-dimensional (3D) visualization of the volumetric data; these include advanced lung analysis, advanced vessel analysis, cardiac, CT colonography, and the like. These applications rely on the values of the image data (intensity or density) to display 3D rendering of selected anatomies using thresholding techniques to identify them from the remaining data.

Some of these applications are used routinely to screen for cancer in the form of tumors. For example, radiologists search for nodules and polyps in the lung and colon using methodologies such as Advanced Lung Analysis (ALA) and Computed Tomography Colonography (CTC).

Radiologists currently detect nodules in the lung by viewing the axial image slices of the chest. This approach is time consuming and becomes more time consuming with increasing numbers of CT slices. Detection is then followed by a separate analysis for characterization of the nodule with the help of Advanced Lung Analysis's (ALA's) segmentation, volume measurement, and reporting tools. Radiologists will also need to view images generated in the analysis of the nodules. The image views of the viewing function and the analysis function are displayed separately. The radiologist must then toggle between separate displays of the multiple image views relating to the viewing and/or the analysis during the course of an exam. As the number of CT slices increases, the review of all the image views in the various steps of viewing and analysis becomes even more time consuming and cumbersome, as the radiologist must navigate back and forth between the image views multiple times with multiple navigation commands.

Processing algorithms for various review and analysis tools continue to be optimized, reducing processing times for individual tools and algorithms. Concurrent with new detection capabilities, like Digital Contrast Agent (DCA), which have improved times to review and analyze image data, there remains a need to streamline workflow involving viewing and analysis functions that reduces the navigation steps and the need to toggle between multiple views, thereby reducing the time required to complete the exam.

BRIEF DESCRIPTION OF THE INVENTION

In an exemplary embodiment of the invention, an image display system is provided, the image display system including user configurable viewports for the review and analysis of image data. The user configurable viewports include a review viewport and an analysis viewport. The review viewport displays in a review mode, a plurality of image views of the image data. The analysis viewport displays in an analysis mode, a plurality of image views of the image data. The review viewport and the analysis viewport may be configured for simultaneous display of related image data.

In another exemplary embodiment, a method of displaying image data is provided, the method including selecting the image data to be reviewed and analyzed and displaying the image data in a review viewport configured for displaying a plurality of image views in a review mode. A nodule is marked in the review viewport. The method further includes analyzing the image data for the marked nodule and display analysis results in an analysis viewport configured for displaying a plurality of image views in an analysis mode. The review viewport and the analysis viewport are simultaneously displayed for related image data.

In another exemplary embodiment, a computer data storage device including computer readable program code is provided. The computer readable program code is configured for executing a method of displaying image data for review and analysis.

BRIEF DESCRIPTION OF THE DRAWINGS

Referring to the exemplary drawings wherein elements are numbered alike in the several Figures.

DETAILED DESCRIPTION OF THE INVENTION

Disclosed herein in the exemplary embodiments are a system and methodologies that enable a streamlined workflow for the review and analysis of acquired data from imaging systems, with reference to a computed tomography (CT) or positron emission tomography (PET) imaging systems. While an exemplary system and methodology of reviewing and analyzing such data is disclosed with reference to a computed tomography (CT) imaging system, it will be appreciated that such disclosure is illustrative only, and it should be understood that the method and system of the disclosed invention may readily be applied to other imaging systems, such as Magnetic Resonance Imaging (MRI), X-ray or ultrasound systems. It should further be noted that the exemplary embodiments include identification, analysis and comparison of suspect lung nodules, which may have application in a variety of imaging fields including, but not limited to vessel analysis, colon and heart vessel segmentation, industrial evaluation or inspection systems, or essentially wherever detailed or small features need to be detected, that use the imaging technology described above.

Radiologists currently detect nodules in the lung by manually viewing axial slices of the chest in one presentation of the image data. As the number of CT slices grows, the time demand on the radiologist increases with the CT slices to be reviewed. The review, or detection step, is followed by an analysis of identified nodules, in another presentation of the image data. User configurable viewports in exemplary embodiments of the invention provide displayable viewports in a review mode and in an analysis mode of image views of image data. The viewports are simultaneously displayed such that a radiologist would not be required to view separate presentations of the image data from the viewing and the analysis functions. The presentations may be synchronized allowing a positional indication of the nodule in multiple views, across the viewing and analysis functions, to be displayed. Presentations of data across multiple exams and data sets may also be simultaneously displayed, synchronized and registered to further streamline the viewing and analysis functions of imaging systems.

Figure 1:
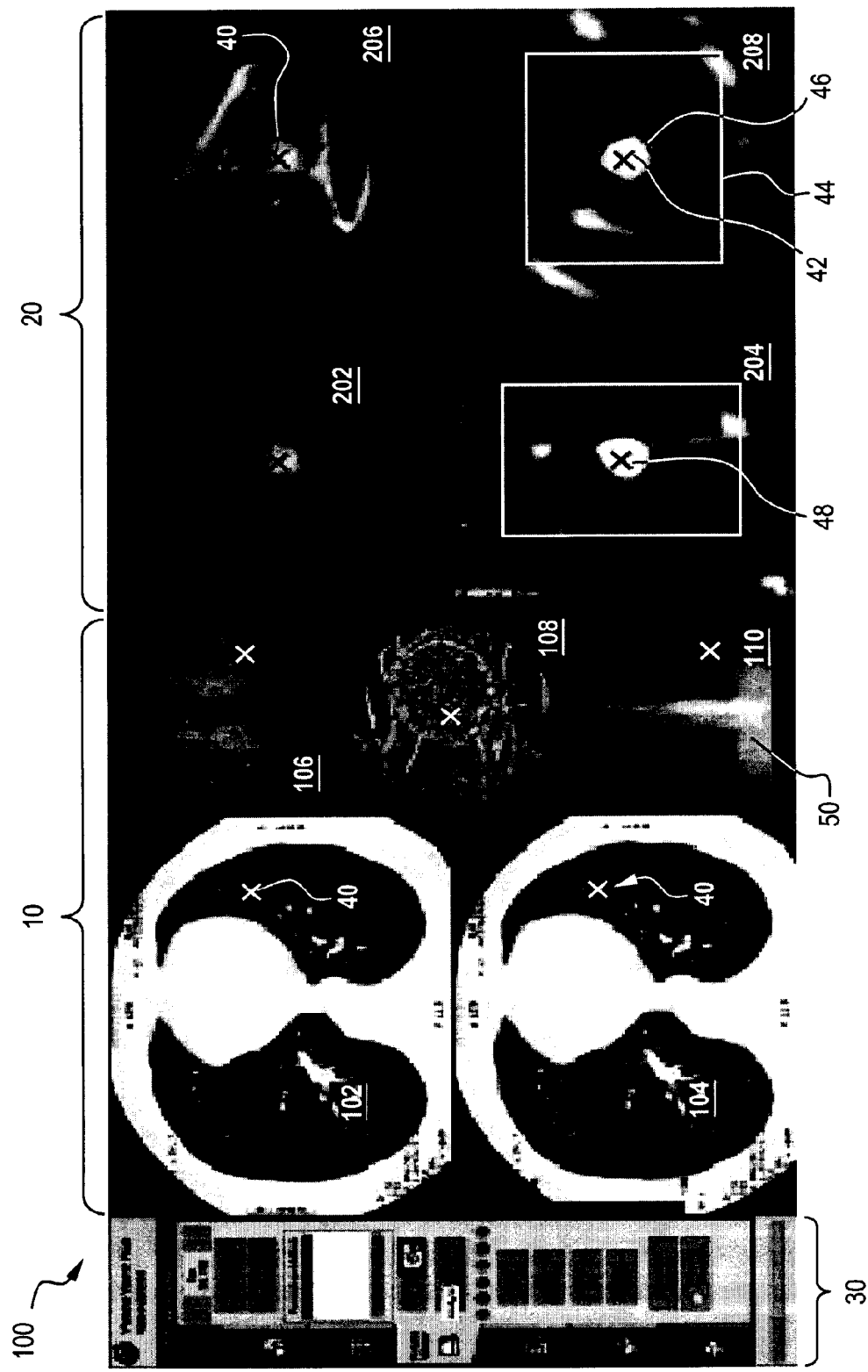
FIG. 1 shows an exemplary embodiment of a digitized image of a medical data display including viewports displaying image views according to an embodiment of the invention.

Referring now to FIG. 1, an exemplary embodiment of an image display system 100 including a review viewport 10 and an analysis viewport 20 is depicted. The review viewport 10 includes multiple image views 102, 104, 106, 108 and 110 of a set of image data. The analysis viewport 20 includes multiple image views 202, 204, 206, and 208 of a set of the image data. Both the review viewport 10 and the analysis viewport 20 may be configured for simultaneous display of related image data.

FIG. 1 shows the review viewport 10 displayed on the left of the analysis viewport 20. A user may configure the review viewport 10 and/or the analysis viewport 20 to display the views 102, 104, 106, 108, 110, 202, 204, 206, and 208 in any of a number of positions within their respective viewport. In alternative embodiments, the analysis viewport 20 may be configured to be displayed to the left of the analysis viewport 20.

Depicting a left-right configuration of the review viewport 10 and the analysis viewport 20 in FIG. 1 is presented for illustration purposes only. The review viewport 10 and the analysis viewport 20 may also be configured for displaying viewports in a top-bottom configuration.

Figure 2:
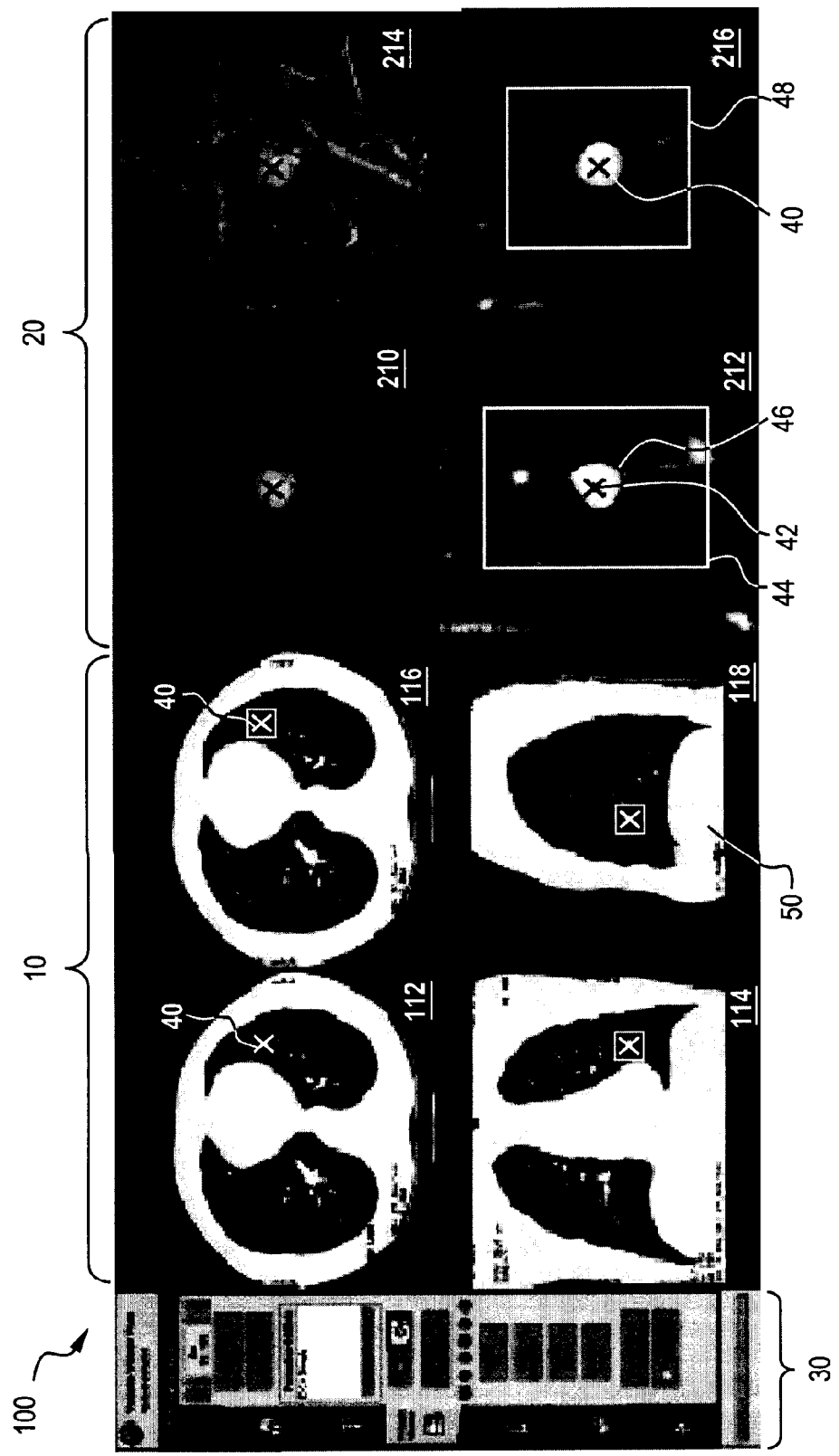
FIG. 2 shows another exemplary embodiment of a digitized image of a medical data display including viewports displaying image views according to an embodiment of the invention.

The review viewport 10 may include image views that display a region of an anatomical object 50 that may have a nodule 40 located therein. Referring to FIGS. 1 and 2, for example, views 102 and 112 display an axial source image of an axial slice from a CT lung scan with an nodule 40. Views 104 and 116 show a thicker maximum intensity projection (MIP) image of view 102 with the nodule 40. "Thicker," as used here, refers to an MIP over a thicker slice than the native slice thickness in view 102. View 106 shows a global three-dimensional maximum intensity projection of the segmented lung region and view 110 shows an x-ray coronal ray sum projection of a patient's lung region, both having the nodule 40. View 114 shows a coronal reformat view and view 118 shows a sagittal reformat view. In exemplary embodiments, the review viewport 10 may be configured to display a region of the anatomical object 50 that contains more than one nodule 40.

In a relative sense, the review viewport 10 may be considered to include "broader" views, such as to provide a perspective view of the nodule 40 in a surrounding anatomical region, the nodule 40 relative to a larger region of the anatomical object 50 or a region with more than one nodule 40. Referring to FIGS. 1 and 2, views 106, 110, 114 and 118 show the nodule 40 with respect to a larger region of the lung of a patient. Views 102, 104, 108, 112 and 116 show the nodule 40 and the region generally surrounding the nodule 40. Essentially, the views 102, 104, 106, 108, 110, 112, 114, 116 and 118 are displayed in a "review mode" allowing a clinician or radiologist to "review" displayed images of marked nodules and/or the anatomical region relative to the marked nodules based on the image data in support of their diagnosis or analysis of the anatomical object 50.

In exemplary embodiments, the review viewport 10 may be configured for synchronized display of the image views. Referring to FIG. 1, for example, if the image in one of the views 102, 104, 106, 108 and 110 were orientated into a different position, a subset of the images in the remaining views may be moved commensurately with the image in the one view. The synchronized display includes more than one of the image views 102, 104, 106, 108 and 110 of the review viewport 10.

In another exemplary embodiment, the review viewport 10 may be configured to display an indicator identifying the nodule 40 in corresponding locations in the views 102, 104, 106, 108 and 110. Referring to FIGS. 1 and 2, each of the views 102, 104, 106, 108, 110, 112, 114, 116 and 118 has the nodule 40 indicated at the appropriate position relative to image in the view. For example, in FIG. 1, both views 106 and 110 show the nodule 40 indicated in the right side of the lung region. In alternative embodiments, the indication 48 for the nodule 40 may be displayed in a subset of the views 102, 104, 106, 108 and 110. More than one of the nodule 40 may be indicated in the image views of the review viewport 10, as it is feasible that there may exist more than one of the nodule 40 in the anatomical region being displayed.

In exemplary embodiments, the review viewport 10 may be configured to allow marking or selection of the nodule 40. The selecting of the nodule 40 may be performed by the image display system 100 or by the user. For example, the user may mark the nodule 40 by a navigation or command step provided by the image display system 100, such as in the review viewport 10.

In other exemplary embodiments, the image display system 100 may include a tool, such a digital contrast agent (DCA), for identifying the nodule 40. Further description of DCA will be later discussed in more detail. The DCA may provide an indication in the review viewport 10 of the nodule 40 location with respect to the anatomical object 50 or region displayed. The DCA may also be configured to allow selection of a size of the DCA to further provide customization of the image display system 100 review and analysis functions. The review viewport 10 or the analysis viewport 20 may be configured to allow the selection of the size of the DCA to further customize the viewports and the data display system.

In alternative embodiments, nodules 40 may be selected by a combination of the image display system 100 and the user's selection. For example, the DCA may provide an indicator 48 at the location of a suspect nodule based on settings of the DCA. Essentially, DCA may be activated on any viewport. In exemplary embodiments, the DCA response may be displayed as a red colored object. In alternative embodiments, indicator 48 may show the segmentation of a nodule in the coronal, sagittal, or transaxial viewport, and is unrelated to DCA.

DCA is a method for highlighting spherical or cylindrical objects in a response of the DCA, aiding the user in locating suspicious objects or nodules. In exemplary embodiments, this method may set an effective filter threshold size, for instance, in millimeters of diameter, for all DCA objects and only show those objects relative to the selected size. For example, only DCA objects in the DCA response may be displayed that are larger than the set threshold, but smaller than a maximum threshold. The maximum threshold may be determined by the user or may be the size of the anatomical object 50, such as an organ, relative to which the nodules are being reviewed and analyzed. In alternative embodiments, the DCA objects displayed may include only those which are of a size equal to or less than the set threshold.

The setting of the effective size may be done by a preference setting in the DCA tool, or be changed interactively using user interface controls. The DCA filter essentially compares the selected size with the DCA objects and filters all those objects relative to the set size. For example, the effective volume of the detected objects (e.g. the volume of all the connected components of the DCA response) may be calculated and compared to what the effective spherical value would be based on the effective filter size.

The user may then review the suspect nodule to make a determination if the suspect nodule should be further analyzed. The user may then mark the suspect nodule for further analysis by any of a number of commands or tools provided by the image data system 100, such as providing an indicator 48. Advantageously, using tools to assist the user in identifying nodules may reduce the time required to complete a review and analysis of the image data. Additionally, the accuracy of the identification of the nodules may be improved.

Referring to FIG. 1, the analysis viewport 20 may include image views 202, 204, 206 and 208 that display the nodule 40 in a more detailed or magnified view. In exemplary embodiments, the views 202, 204, 206 and 208 may also include a region or other anatomical features immediately surrounding the nodule 40. In yet other exemplary embodiments, the analysis viewport 20 may be configured to display a subset of the multiple nodules 40 that may be displayed in the review viewport 10, as discussed above.

Referring to FIGS. 1 and 2, for example, views 202 and 210 display a nodule view of the nodule 40 alone, so as to provide a sense of the shape, location, and composition of the nodule 40. Image view 202, 206, 210 and 214 also display analysis parameters including nodule characteristics and volume parameters in the text around the periphery of the image view 202. Views 206 and 214 show a nodule shutter view of the nodule 40 and surrounding blood vessels in the immediate area of the nodule 40. Views 204 and 212 display an axial contour and image views 208 and 216 show a sagittal contour of the segmented nodule in axial and sagittal views.

Essentially, the views 202, 204, 206, 208, 210, 212, 214 and 216 are displayed in an "analysis mode" providing information regarding the nodule 40 to the clinician or radiologist to in further support of their diagnosis or analysis of the nodule 40 and the anatomical object 50.

In contrast to the review viewport 10, in a relative sense, the analysis viewport 20 may be considered to include "localized" views of the anatomical object 50, such as to provide a view of the nodule 40 in a detailed or magnified view or as a single object being a subset of a larger identified group of nodules 40. These "localized" views may include a region immediately surrounding the nodule 40 or may include anatomical features in the immediate region around the nodule 40, as discussed above.

In exemplary embodiments, the analysis viewport 20 may be configured for synchronized display of the image views. Referring to FIG. 1, for example, if the image in one of the views 202, 204, 206 and 208 were manipulated into a different orientation, a subset of the images in the remaining views may be moved commensurately with the image in the one view. The synchronized display includes more than one of the image views 202, 204, 206 and 208 of the analysis viewport 20.

In another exemplary embodiment, the analysis viewport 20 may be configured to display an indicator 48 identifying the nodule 40 in corresponding locations in the image views. Referring to FIG. 1, each of the views 202, 204, 206 and 208 has the nodule 40 indicated at the appropriate position relative to the images in the other views 202, 204, 206 and 208. In alternative embodiments, the indication may be displayed for the nodule 40 in a subset of the views 202, 204, 206 and 208.

In exemplary embodiments, the review viewport 10 and the analysis viewport 20, as shown in FIG. 1, may be configured for synchronized display of the views 102, 104, 106, 108, 110, 202, 204, 206 and 208. For example, if the image in one of the views 102, 104, 106, 108, 110, 202, 204, 206 and 208 were orientated into a different position, a subset of the remaining views may be moved commensurately with the image in the one view.

In other exemplary embodiments, if a different nodule 40 than the one currently being displayed in the review viewport 10 and the analysis viewport 20 were selected by the user, the display views 102, 104, 106, 108, 110, 202, 204, 206 and 208 may be refreshed to show the different nodule 40 in respective review mode in the review viewport 10 and in and analysis mode in the analysis viewport 20. The synchronized display includes at least one image view 102, 104, 106, 108 and 110 of the review viewport 10 and at least one image view 202, 204, 206 and 208 of the analysis viewport 20.

The user is allowed to simultaneously observe a totality of the images of the medical data in their "review" and "analysis" modes without having to toggle between the images or the modes. Advantageously, the number of user navigation commands or steps may be reduced, along with the time to complete the review and the analysis functions of the examination. Additionally, the quality of the diagnosis may be improved as the user may spend less time navigating through the image display system 100, the user now being allowed to concentrate on the review and analysis of the image data.

In another exemplary embodiment, the review viewport 10 and the analysis viewport 20 may be configured to display an indicator 48 identifying the nodule 40 in corresponding locations in the image views. Referring to FIG. 1, each of the views 102, 104, 106, 108 and 110 has the nodule 40 indicated at the appropriate position relative to the images in the other views 202, 204, 206 and 208. In alternative embodiments, the indication may be displayed in a subset of images or in a subset of the views 102, 104, 106, 108, 110, 202, 204, 206 and 208.

The indicator 48 of the nodule 40 in the review viewport 10 and the analysis viewport 20 may be displayed by any of a number of visual display means, including, but not limited to, color highlighting, an indicator box 44, a cross hair 42, outlining, a textual marking, an action marking an audible signal or any combination including at least one of the foregoing. Color highlighting may include any of a number of colors to visually distinguish the nodule 40 location from the surrounding region. The textual marking may include an alphanumeric character. For example, characters forming a word or label used to index the nodule 40 for future reference in the examination is contemplated. The action marking may include the indication of visually "moving" in some manner, such as blinking, rotating or pulsing. The audible signal may include a bell, a buzz, a spoken word, or the like, as well as any signal suitable for the purpose disclosed herein.

In exemplary embodiments, a single indicator 48 may be displayed to indicate the nodule 40. In alternative embodiments, a combination of the indicators 48 may be used indicate the nodule 40. Referring to FIG. 1, views 106, 108 110, 202 and 206 illustrate the nodule 40 by an X-shaped cross hair 42. Views 102 and 104 indicate the nodule 40 by the X-shaped crosshair 42 and an indicator box 44. Views 204 and 208 have the X-shaped crosshair 42, and the indicator box 44 with the boundary of the nodule 40 outlined 46 in a darker line to contrast with the surrounding region.

In other exemplary embodiments, the image display system 100 may be configured to display and operate a utility viewport 30. The utility viewport 30 may include navigation functions and reporting and/or file commands that are used with the review viewport 10 and/or the analysis viewport 20. For example, the user may desire to save image data, image views, analysis results and diagnosis comments in a DICOM SR format (from Digital Imaging and Communications in Medicine), a standard developed by ACR-NEMA (American College of Radiology—National Electrical Manufacturer's Association) for communications between medical imaging devices. A report may be exported in DICOM SR format and the indicated nodules may be saved into an RTSS file format, a standard within DICOM for radiation therapy. The analysis viewport 20 may also be configured to display and/or operate any of a number of utility functions discussed above.

In exemplary embodiments, the review viewport 10 may be configured to display any of a number of image views of the image data, including, but not limited to an axial view, a coronal view, a sagittal view, a shutter (three-dimensional) view, or the like, or any "broader" perspective view suitable for the purpose described herein. The review viewport 10 may also be configured to display and/or operate bookmarking, classification of the nodule 40, or any of a number of utility functions discussed above.

In exemplary embodiments, the analysis viewport 20 may be configured to display any of a number of image views associated with analysis tools, including, but not limited to, bookmarking, segmentation, volume rendering, volume computations, growth analysis, dimensional analysis, total volume of a nodule, percent volume of the nodule to the volume of a region of an anatomical structure, classification of the nodule 40, or the like, or any "localized" perspective views suitable for the purpose describe herein.

Analysis tools may include a method of fully automated trachea and lung segmentation from computer tomography, such as is described in U.S. patent application Ser. No. 11/085,736 filed Mar. 25, 2005 and commonly assigned. Lung segmentation allows focus on the lung area only and is a critical preprocessing step for several other tools in advanced lung analysis (ALA) such as, the digital contrast agent (DCA) algorithm, the automated registration algorithm and visualization of the lung shape, including the ability to adjust the visualization of cross-slices allowing concentration on the lung region.

Another analysis tool may include methods of visualization and detection of anatomical shapes using post processing of three-dimensional filtering for suppression of false response such as is described in U.S. patent application Ser. No. 10/961,245 filed on Oct. 8, 2004 and commonly assigned. Here, disparate responses (e.g. spherical and cylindrical) may be post-processed using anatomical information to minimize the cross pollution of responses and/or using response classification algorithms to reduce the size of the cross pollution followed by a visualization process that displays the responses.

Another analysis tool may include a real-time method for anatomical shape filtering and visualization of any three-dimensional volumetric dataset such as is described in U.S. patent application Ser. No. 10/709,355 filed Apr. 29, 2004 and commonly assigned. An algorithm for shape filtering methods may be used to enhance spherical and cylindrical shapes in CT scans, such as is related to DCA.

Another analysis tool may include real-time implementation of shape filtering methods on anisotropic volumetric datasets such as is described in U.S. patent application Ser. No. 11/079,694 filed Mar. 14, 2005 and commonly assigned.

Here, filtering methods may be used for the purpose of tracking longitudinal changes in shape and size of various anatomies and pathologies.

As previously discussed, embodiments of the invention may include one or more of the aforementioned analysis tools.

Figure 3:
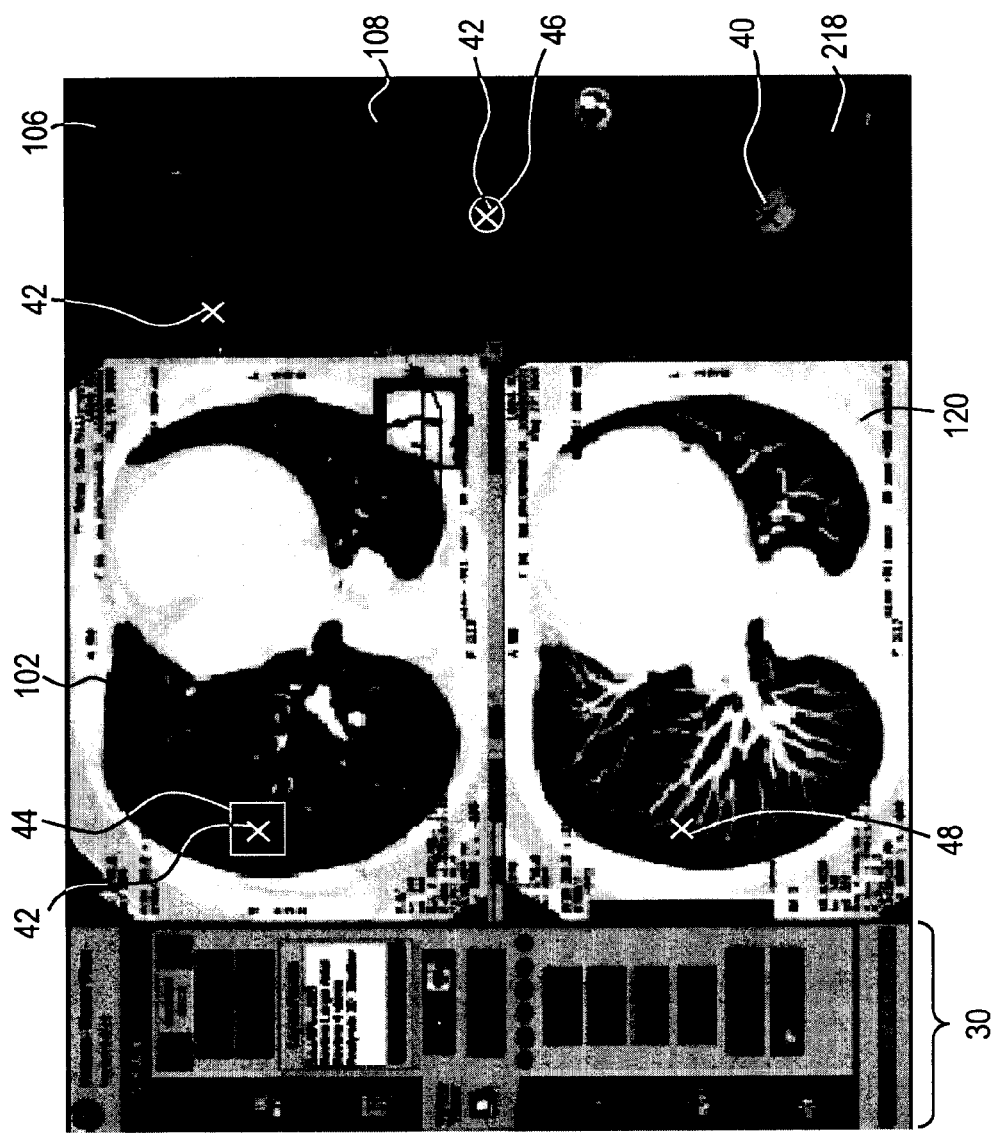
FIG. 3 shows another exemplary embodiment of a digitized image of a medical data display including viewports displaying image views according to an embodiment of the invention.
Figure 4:
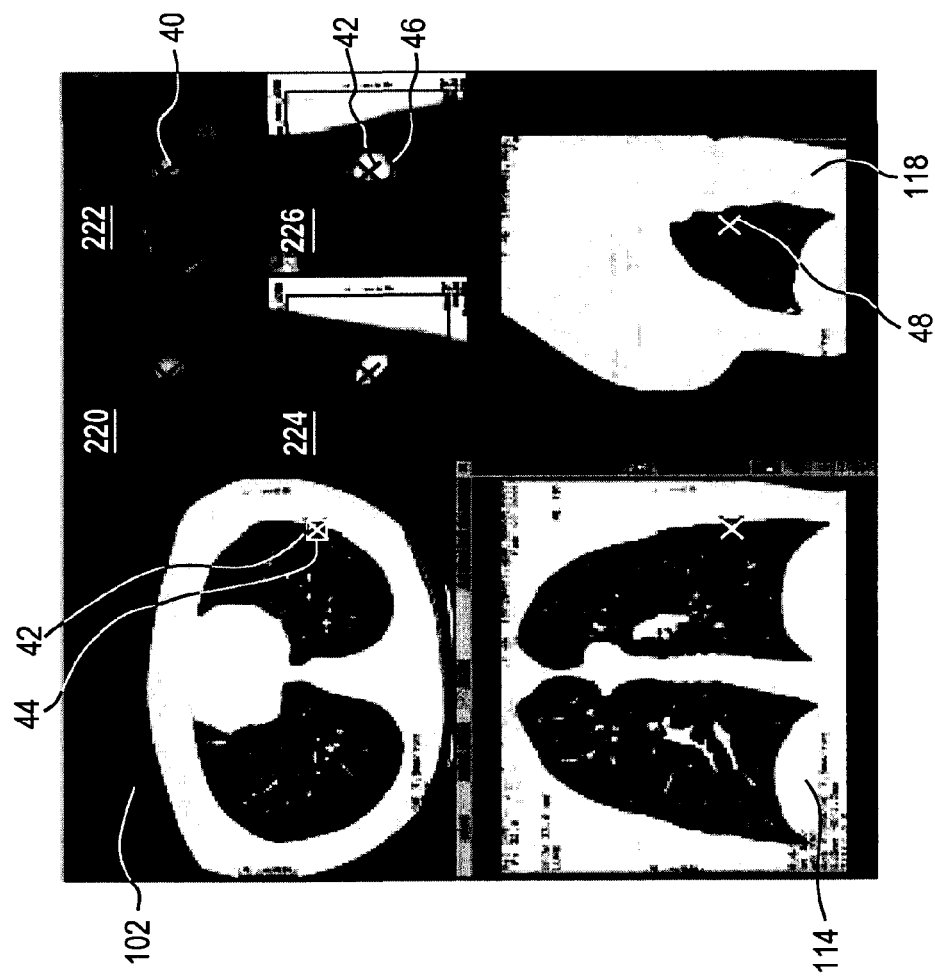
FIG. 4 shows another exemplary embodiment of a digitized image of a medical data display including viewports displaying image views according to an embodiment of the invention.

In other exemplary embodiments, the image data display system 100 may be configured to display "broader" image views of the review viewport 10 and "localized" image views of the analysis viewport 20 in a variegated configuration. For example, image views of the review viewport 10 and the analysis viewport 20 may be alternately displayed or grouped as the user chooses to configure the image display system. Referring to FIG. 3, a single image view 218 of the analysis viewport 20 is arranged with image views 102, 106, 108 and 120 of the review viewport 10. FIG. 4 shows an alternative embodiment of the image display system 100, where a group of image views 220, 222, 224 and 226 of the analysis viewport 20 is configured to be displayed at the top right of the display layout. Review views 102, 114 and 118 of the review viewport 10, are displayed relative to the group of image views of the analysis viewport 20. Essentially, the user may configure the review viewport 10 and the analysis viewport 20 to display any of a number of image views of the data so as to efficiently perform the review and analysis functions of an examination.

Figure 5:
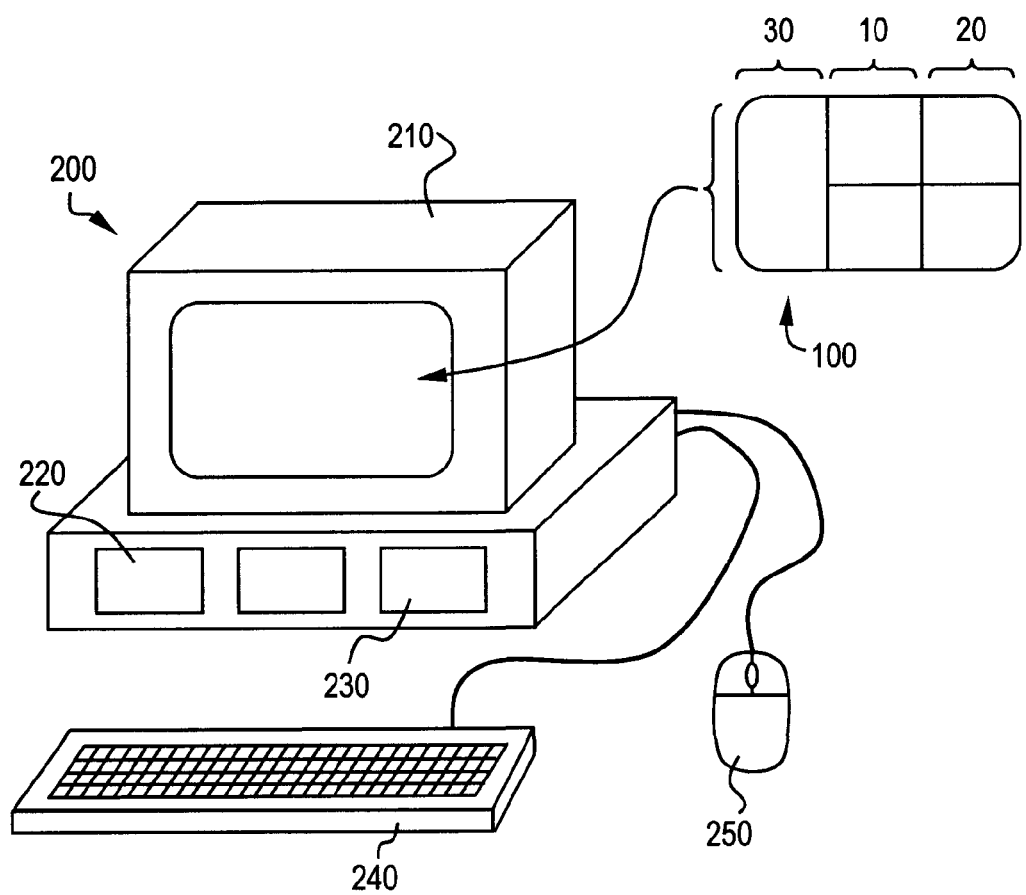
FIG. 5 shows an exemplary embodiment of an image display system including a data storage device and display means according to an embodiment of the invention.

The image display system 100 may further include a single visual display means or multiple visual display means. The single visual display means may be referred to as "single head layout" and the multiple visual display means as "dual head layout." FIGS. 1 and 2 show exemplary embodiments of a dual head layout. FIGS. 3 and 4 show exemplary embodiments of the single head layout. FIG. 5 shows an exemplary embodiment of a visual display means 210 and a data storage device 200 according to an embodiment of the invention. The image display system 100 and the user configurable viewports 10, 20 and 30 are indicated as being displayed on the visual display means 210.

In another exemplary embodiment, the image data may include a first set of data and a second set of data. The first set of data is acquired prior to the second set of data, such as from two different exams. The image data display system 100 may be further configured to register the image data across the multiple exams. Advantageously, selected regions of the anatomical object 50 that may include a nodule 40 are synchronized allowing the user to evaluate a change in the nodule 40. The review viewport 10 or the analysis viewport 20 may be configured to display registered image views from the multiple exams.

FIGS. 1-4 are presented depicting a configuration of the review viewport 10 and the analysis viewport 20 for a single exam for illustration purposes only. The review viewport 10 and the analysis viewport 20 may also be configured for displaying image views from both a first set and a second set of image data.

An exemplary embodiment of a method of displaying image data is also provided. The method includes selecting the image data to be reviewed and analyzed. As discussed above, the image data may include two data sets from multiple exams or data acquisitions. In alternative embodiments, selecting the image data may include configuring a digital contrast agent (DCA) to define a size of the DCA.

The image data is displayed in a review viewport 10 configured for displaying a first set of image views in a review mode. The displaying images in the review viewport 10 may include synchronizing the image views in the review viewport 10. In exemplary embodiments, the displaying of the image data in the review viewport 10 may include displaying indicators 48 of the nodule 40. In alternative embodiments, the indicators 48 may be provided by the DCA, the user or both.

A nodule may be marked in the review viewport 10 by an image display system 100 tool 260 such as the digital contrast agent (DCA), a computer program or an algorithm. The user may also mark the nodule in the review viewport 10 using appropriate navigation keystrokes or commands via input means 240 or 250 to a data storage device 200 as shown in the exemplary embodiment of FIG. 5.

The image data for the marked nodule is analyzed by the image display system 100. The analysis of the image data may be performed automatically by the image display system 100 or the user may be required to initiate the analysis by defined keystrokes or commands using input means 240 or 250 as shown in FIG. 5. In exemplary embodiments, the analysis function performed on the image data may be preset in the image display system 100 or may be selectively chosen by the user.

Results of the analysis function are displayed in an analysis viewport 20 configured for displaying a set of image views in an analysis mode. The displaying images in the analysis viewport 20 may include synchronizing the image views in the analysis viewport 20. In exemplary embodiments, the displaying of the image data in the analysis viewport 20 may include displaying indicators 48 of the nodule 40.

In another exemplary embodiment, the review viewport 10 and analysis viewport are simultaneously displayed for related image data. The simultaneous displaying may include synchronizing the image views in the review viewport 10 and the analysis viewport 20.

In another embodiment, a computer data storage device 200 is provided. The computer storage data device 200 may include storage means 220, such as RAM or other memory device, and a data access means, 230, such as a disk drive. A technical effect of exemplary embodiment is a streamlined workflow involving review and analysis functions that reduce the navigation steps and the need to toggle between multiple image views.

In alternative embodiments, the computer storage device 200 may include computer readable program configured for executing a method of displaying image data. The method includes selecting image data to be reviewed and analyzed, displaying the image data in a review viewport 10 configured for displaying a plurality of image views in a review mode, marking a nodule 40 in the review viewport 10, analyzing the image data for the marked nodule 40, displaying analysis results in an analysis viewport 20 configured for displaying a second plurality of image views in an analysis mode and simultaneously displaying the review viewport and the analysis viewport 20.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the appended claims.

What is claimed is:

1. An anatomical image data display system having a graphical display comprising:
   user configurable viewports for the review and analysis of image data, the image data comprising first acquired anatomical image data from a first exam and a second acquired anatomical image data from a second exam, wherein the first acquired anatomical image data and the second acquired anatomical image data include a nodule;
   the viewports comprising:
   a review viewport on the graphical display for displaying in a review mode a first plurality of image views of the first acquired anatomical image data and the second acquired anatomical image data, wherein the review viewport is configured to display an indicator comprising a cross hair and at least one other visual display means on the graphical display to mark the nodule;
   an analysis viewport on the graphical display for displaying in an analysis mode a second plurality of image views of the first acquired anatomical image data and the second acquired anatomical image data,
   wherein the review viewport and the analysis viewport are configured for simultaneous and synchronized display of the anatomical object to allow evaluation of changes in the nodule from the first exam to the second exam, wherein changes in orientation of one of the plurality of views of one of the first and second acquired anatomical image data in one portion of at least one of the review viewport and the analysis view port results in corresponding changes in orientation to another of the plurality of views of one of the first and second acquired anatomical image data in another portion of at least one of the review viewport and the analysis viewport;
   wherein the review viewport, the analysis viewport or both are further configured to display registered image views, the registered image views comprising a region including the nodule synchronized between the first acquired image data and the second acquired image data;
   further comprising a digital contrast agent (DCA) including a DCA response, the digital contrast agent configured to allow selection of a first size threshold of the DCA response, wherein the review viewport is further configured to allow a user selection of the first size threshold of the DCA, wherein the first size threshold allows for selective display of the DCA response relative to the first size threshold, and wherein the displayed DCA response is larger relative to the first size threshold and smaller relative to a second size threshold,
   wherein the marking of the nodule comprises the DCA providing the indication of the nodule in the image data.

2. The image data display system of claim 1, wherein the review viewport is configured for synchronized display of a first set of image views, the first set of image views including at least two image views of the first plurality of image views.

3. The image data display system of claim 2, wherein the review viewport is configured to display the indicator for identifying the nodule at corresponding positions in each of the image views of the first set.

4. The image data display system of claim 1, wherein the review viewport is configured to allow marking of the nodule in the first plurality of image views.

5. The image data display system of claim 4, further comprising the marking of the nodule comprising the user providing the indication of the nodule.

6. The image data display system of claim 1, wherein the analysis viewport is configured for synchronized display of a second set of image views, the second set of image views including at least two image views of the second plurality of image views.

7. The image data display system of claim 6, wherein the analysis viewport is configured to display the indicator for identifying a nodule at corresponding positions in each of the image views of the second set.

8. The image data display system of claim 1, wherein the review viewport and the analysis viewport are configured for synchronized display of a third set of image views, the third set of image views including at least one image view from the first plurality of image views and at least one image view from the second plurality of image views.

9. The image data display system of claim 8, wherein the review viewport and the analysis viewport are configured to display the indicator for identifying a nodule at corresponding positions in each of the image views of the third set.

10. The anatomical image data display system of claim 1, wherein the at least one other visual display means comprises an indicator box.

11. The anatomical image data display system of claim 1, wherein the at least one other visual display means comprises a color highlighting.

12. The anatomical image data display system of claim 1, wherein the at least one other visual display means comprises an outline.

13. The anatomical image data display system of claim 1, wherein the at least one other visual display means comprises a textual marking.

14. The anatomical image data display system of claim 1, wherein the analysis viewport is configured to display a second indicator marking the nodule on the graphical display, wherein the second indicator comprises the same visual display means as the indicator used in the review viewport.

15. A method of displaying image data for review and analysis, the method comprising:
    selecting the image data to be reviewed and analyzed, the image data comprising first acquired anatomical image data from a first exam and second acquired anatomical image data from a second exam, wherein the first acquired anatomical image data and the second acquired anatomical image data include a nodule;
    displaying the first acquired anatomical image data and the second acquired anatomical image data in a review viewport configured for displaying a first plurality of image views of the first acquired anatomical image data and the second acquired anatomical image data marking the nodule in the review viewport;
    analyzing the image data for the marked nodule;
    displaying analysis results in an analysis viewport configured for displaying a second plurality of image views in an analysis mode;
    synchronously and simultaneously displaying the review viewport and the analysis viewport for related image data of the nodule synchronized between the first acquired anatomical image data and the second acquired anatomical image data to allow evaluation of changes in the nodule from the first exam to the second exam wherein changes in orientation of one of the first plurality of image views of the first acquired anatomical image data in one portion of at least one of the review viewport and the analysis view port results in corresponding changes in orientation to one of the second plurality of image views of the second acquired anatomical image data in another portion of at least one of the review viewport and the analysis viewport, and further comprising marking the nodule in the review viewport and the analysis viewport with an indicator comprising a cross hair and at least one other visual display means;
    wherein the selecting the image data comprises a user configuring a size threshold of a digital contrast agent (DCA), the size threshold allowing selective displaying of nodules larger than the size threshold and smaller than a maximum threshold,
    wherein marking the nodule comprises displaying the indicators of the nodules, the indicators generated by the digital contrast agent (DCA).

16. The method of claim 15, further comprising the marking of the nodule comprises displaying indicators of the nodule, the indicators created by the user.

17. The method of claim 15, wherein the marking the nodule to be analyzed comprises a digital contrast agent (DCA) indicating a nodule, a user indicating the nodule or both.

18. The method of claim 15, wherein the simultaneous displaying the review viewport and the analysis viewport comprises synchronizing the first plurality of image views and the second plurality of image views.

19. A computer data storage device, said computer data storage device including computer readable program code, the computer readable program code configured for executing the method of claim 15.

* * * * *